United States Patent [19]
Fallick

[11] Patent Number: 5,945,447
[45] Date of Patent: Aug. 31, 1999

[54] TOPICAL VITAMIN C PREPARATION

[75] Inventor: Harry Fallick, King of Prussia, Pa.

[73] Assignee: Fallien Cosmeceuticals Ltd, King of Prussia, Pa.

[21] Appl. No.: 09/013,628

[22] Filed: Jan. 26, 1998

Related U.S. Application Data

[63] Continuation-in-part of application No. 08/646,935, May 8, 1996, Pat. No. 5,846,996.

[51] Int. Cl.⁶ .................................................... A61K 31/34
[52] U.S. Cl. ............................................ 514/474; 514/63
[58] Field of Search ...................................... 514/474, 63

[56] References Cited

U.S. PATENT DOCUMENTS 5,587,149  12/1996  Punto et al. ............................... 424/59

*Primary Examiner*—Zohreh Fay
*Attorney, Agent, or Firm*—John Lezdey & Assoc.

[57] ABSTRACT

A topical preparation containing about 5 to 15% by weight of ascorbic acid; about 5 to 15% by weight of water; a mixture of high and low molecular weight polyethylene glycol and silicone or vegetable oil. The preparation is placed into a package in unit dosage form under the atmosphere of an inert gas so as to be substantially free of oxygen.

10 Claims, No Drawings

TOPICAL VITAMIN C PREPARATION

RELATED APPLICATION

This application is a continuation-in-part of application Ser. No. 08/646,935 filed May 8, 1996 now U.S. Pat. No. 5,846,996.

FIELD OF THE INVENTION

The present invention relates to topical preparations having a higher amount of active and stable vitamin C (L-ascorbic acid) for delivery to the skin. More particularly, there is provided a vitamin C preparation having a higher amount of water and vitamin C which is packaged in an inert atmosphere.

BACKGROUND OF THE INVENTION

L-ascorbic acid has many known biological functions from enzymatic co-factor to "sparing" agent against vitamin E depletion. See, for example, Englard and Seifter, "The Biochemical Functions of Ascorbic Acid", Ann. Rev. Nutri. 6:365–406, (1986); Kunert and Tappel, "The Effect of Vitamin C on in vivo Lipid Peroxidation in Guinea Pigs as Measured by Pentane and Ethane Production, *Lipids;* 18:271–74 (1983). The latter function may partly account for its "anti-oxidant" status. Additionally, at higher concentrations, ascorbic acid is known to react with both the superoxide and hydroxyl radicals. Superoxide and the subsequently generated hydrogen peroxide and hydroxyl radical are oxygen-containing free radicals now known to be generated in vivo under a variety of normal and pathological conditions. Quite simply, these radicals have been implicated as causative agents for everything from sunburn to aging. These radicals destroy lipid membranes, break down DNA, inactivate enzymes and so forth. An immense amount of work has been done in the last two decades documenting the deleterious behavior of oxygen radicals. Several recent texts on the subject include:

*Oxy-radicals in Molecular Biology & Pathology,* D. Cerutti, I. Fridovich, J. McCord, eds., (Alan R. Liss, Inc. New York, 1988);

*Biological Role of Reactive Oxygen Species in Skin,* O. Hayaishi, S. Inamura, Y. Mayachi, eds. (Elsevier Press, New York, 1987);

*Free Radicals Aging and Decenerative Diseases,* J. E. Johnson, Jr., R. Walford, D. Harmon, J. Miguel, eds. (Alan Liss, Inc., New York, 1986);

*Free Radicals in Biology and Medicine,* B. Halliwell and J. M. C. Gutteridge, eds. (Clarendon Press, Oxford, 1985); and

*Oxidative Stress* Helmut Sies, ed. (Academic Press, 1985).

Also addressing the subject are several symposia, including "Oxygen Radicals and Tissue Injury" Proceedings from an Upjohn Symposium (April, 1987); and "Oxygen Free Radicals", Proceedings from National Heart, Lung & Blood Institute (National Institute of Health, Washington, D.C., December 1987).

L-ascorbic acid rapidly undergoes oxidative degradation due to the ascorbate anion's propensity to act as a reductant. The one-election oxidation product (dehydroascorbate free radical) tends to disproportionate, forming another ascorbate molecule and the two-electron oxidation product, dehydroascorbate, which is extremely unstable in aqueous solutions and breaks down to ultimately form species such as L-threonic acid and oxalic acid which are not beneficial for treating skin conditions.

The literature describes ascorbic acid compositions formed by using a very low weight percent ascorbic acid, or a nonaqueous solvent, or by using derivatives of ascorbic acid, usually in a solution buffered to a pH above 4.0. See, for example, Takashima et al, "Ascorbic Acid Esters and Skin Pigmentation," Am. Perfumer & Cosmetics 86: 29 (July 1971) (esterifying the hydroxyl group to form ascorbic acid-3-phosphate and maintaining an alkaline pH); Ciminera and Wilcox, "Stable Ascorbic Acid Solution for Parenteral Use", J. Am. Pharm. Assoc. Sci. Ed. 35:363 (1946) (buffering an aqueous solution with an alkaline sodium salt). See also U.S. Pat. No. 4,367,157 which discloses stabilizing an aqueous ascorbic acid solution by adding monothioglycerol and maintaining the pH between 4 and 7; U.S. Pat. No. 2,400,171 which discloses stabilizing ascorbic acid by converting it to its calcium or zinc salt and preferably maintaining the pH at 7 to 7.3; U.S. Pat. No. 2,442,461 which discloses stabilizing calcium ascorbate by adding an aliphatic thiocarboxylic acid and maintaining the pH between 5.2 and 5.6; U.S. Pat. No. 2,585,580 which discloses stabilizing ascorbic acid with thio-sugars and maintaining the pH between 4.0 and 6.5; and U.S. Pat. No. 4,372,874 which discloses actually removing the water to below 0.5 wt % by using a desiccant. In many cases, these techniques have been successful in obtaining stable solutions but have been reasonably expensive and have yielded a product with less desirable properties than ascorbic acid in its unmodified form.

The prior art methods of preparing a stable L-ascorbic acid solution are more expensive and require immediate use of the entire package once exposed to air.

Therefore, there is a need for producing unit dosages for single applications without causing degradation of an entire package.

U.S. Pat. No. 5,587,149 to Punto et al. discloses topical vitamin C emulsions which are packaged in gelation capsules. Since they are packaged in capsules, low amounts of water and vitamin C are utilized. To increase solubility without increase in water, mineral oil is utilized. Mineral oil has the disadvantage when used on acne or acne related diseases. Also, some commercial mineral oils contain benzene hydrocarbons.

SUMMARY OF THE INVENTION

The present invention provides a mineral oil free topical preparation having a higher content of L-ascorbic acid and water. More particularly, there is provided a preparation comprising:

A. about 5 to 15% by weight of L-ascorbic acid;

B. about 5 to 15% by weight of water;

C. about 5 to 20% by weight of polyethylene glycol having a molecular weight greater of at least 800;

D. about 5 to 30% by weight of polyethylene glycol having a molecular weight less than 800, said lower molecular weight polyethylene glycol being in an amount greater than the higher molecular weight polyethylene glycol; and E. about 30 to 50% by weight of a silicone or vegetable oil.

Preferably, the preparation contains a mixture of silicone oils.

Advantageously, the preparation contains an antioxidant and is packaged in unit dosage form as a cream or lotion under an atmosphere of an inert gas so as to avoid any substantial oxidation of the preparation and thereby maintain the activity of the ascorbic acid.

It is therefore an object of the present invention to provide a stable L-ascorbic acid solution for topical application.

It is another object of the invention to provide a stable solution of L-ascorbic acid in a unit dosage form having improved shelf life.

DESCRIPTION OF THE PREFERRED EMBODIMENTS

The present invention provides a stable mineral oil free preparation of L-ascorbic acid having greater shelf life. According to the present invention, L-ascorbic acid is dissolved in distilled deionized water together other solvents and ingredients in which an inert gas is passed and the solution has been packaged for single application under oxygen-free conditions. The preparation comprises L-ascorbic acid in an amount of about 5 to 15% by weight, preferably, about 5 to 10% by weight.

The inert gas can be nitrogen, argon, carbon dioxide, or the like. Nitrogen is the most preferred.

The mineral oil free preparation for packaging in unit dosage form comprises:

A. about 5 to 15% by weight, preferably about 5 to 10% by weight of L-ascorbic acid;

B. about 5 to 15% by weight, preferably about 5 to 10% by weight of water;

C. about 5 to 20% by weight, preferably about 6 to 10% by weight of polyethylene glycol having a molecular weight greater than 800;

D. about 5 to 30% by weight, preferably about 12 to 16% by weight of polyethylene glycol having a molecular weight less than 800; and E. about 30 to 50% by weight of silicone oil or vegetable oil.

If desired, an oxygen metabolite scavenger can be added to the solution. Preferred are those oxygen metabolite scavengers which also are beneficial in the treatment of skin diseases. The oxygen metabolite scavengers are present up to about 1% by weight, preferably in a range about 0.1 to 0.5%. Suitable scavengers include glutathione, glutathione peroxidase, bioflavinoids, ceruloplasmin, vitamin E, and the like.

Preferred is glutathione, which has been shown to exhibit anti-viral activity and vitamin E which appears to promote healing and prevents the formation of keloid scars. However, to prepare a solution which includes vitamin E (tocopherol), the vitamin E is first dissolved in tocopherol polyethylene glycol 1,000 succinate, which is available from Eastman Chemical Corporation.

Preservatives such as methyl paraben, 5-bromo-5-nitro-1,3-dioxane and the like, and chelates/sequesterants such as edetic acid (EDTA), pentasodium pentetate and the like may also be included, as well as UV absorbers such as benzene sulfonic acid.

The following examples further illustrate the practice of the invention but are not intended to be limiting thereof. It will be appreciated that the amount to be utilized in the treatment of skin conditions will depend on the type of injury or disease and the degree or stage of the injury or disease.

EXAMPLE 1

A vitamin C containing preparation was prepared by admixing the following ingredients:

| Ingredient | Wt. % | Chemical Name |
|---|---|---|
| DI Water | 10.02 | |
| Sodium Chloride | 0.30 | |
| Hampene 100 | 0.03 | EDTA |
| PEG 400 | 14.00 | Polyethylene Glycol 400 |
| PEG 1000 | 8.00 | Polyethylene Glycol 1000 |
| Pelemol G7A | 7.00 | Glycereth-7 Triacetate |
| Ascorbic Acid | 5.00 | |
| DC 3225C | 15.00 | Cyclomethicone and Dimethicone Copolyol |
| DC 245 | 18.25 | Cyclomethicone |
| DC 556 | 8.00 | Phenyl Trimethicone |
| DC 1401 | 5.50 | Cyclomethicone and Dimethiconol |
| Lipovol GTB | 3.30 | Tribehenin |
| Spheron P-1500 | 2.40 | Silica |
| Dry Flo PC | 1.3 | Aluminum Starch Octylsuccinate |
| Liquipar PE | 0.50 | Mixed parabens |
| Tocopherol Acetate | 1.00 | |
| Germall 115 | 0.3 | Imidazolidinyl Urea |
| Fragrance 61372 | 0.1 | |

EXAMPLE 2

One hundred light impermeable vials of L-ascorbic acid containing 1 ml of solution were prepared by bubbling nitrogen through 100 ml of the preparation of Example 1 and the solution was delivered under a nitrogen atmosphere into the vials. The vials were sealed and stored.

What is claimed is:

1. A package in unit dosage form a mineral oil free topical preparation consisting of:

A. about 5 to 15% by weight of 1-ascorbic acid;

B. about 5 to 15% by weight of water;

C. about 5 to 20% by weight of polyethylene glycol having a molecular weight of at least 800;

D. about 5 to 30% by weight of polyethylene glycol having a molecular weight less than 800, said lower molecular weight polyethylene glycol being present in an amount greater than said lighter molecular weight polyethylene glycol; and E. about 30 to 50% by weight of a silicone or vegetable oil, said package being substantially free of oxygen.

2. The package of claim 1 comprising about 5 to 15% by weight of polyethylene glycol having a molecular weight of about 1000 and about 10 to 20% by weight of a polyethylene glycol having a molecular weight of about 400.

3. The package of claim 1 comprising a mixture of silicone oils.

4. The package of claim 1 including about 0.1 to 1% by weight of imadazolidinyl urea.

5. The package of claim 1 including glycereth 7-triacetate.

6. The package of claim 1 comprising:

A. about 5 to 10% by weight of L-ascorbic acid;

B. about 12 to 16% by weight of polyethylene glycol 400;

C. about 6 to 10% by weight of polyethylene glycol 1000;

D. about 5 to 10% by weight of water; and

E. about 30 to 50% by weight of silicone oil.

7. The package of claim 1 including an antioxidant.

8. A package comprising the preparation of claim 1 in unit dosage form which is substantially free of oxygen.

9. The package of claim 1 including an inert gas.

10. The package of claim 1 including an oxygen metabolite scavenger.

* * * * *